(12) United States Patent
Tidén

(10) Patent No.: US 7,943,625 B2
(45) Date of Patent: May 17, 2011

(54) 2 THIOXANTHINE DERIVATIVES ACTING AS MPO-INHIBITORS

(75) Inventor: Anna-Karin Tidén, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 569 days.

(21) Appl. No.: 11/756,967

(22) Filed: Jun. 1, 2007

(65) Prior Publication Data

US 2008/0221133 A1 Sep. 11, 2008

Related U.S. Application Data

(60) Provisional application No. 60/810,919, filed on Jun. 5, 2006.

(51) Int. Cl.
C07D 473/22 (2006.01)
A61K 31/522 (2006.01)
A61P 25/16 (2006.01)
A61P 25/14 (2006.01)
C07D 233/90 (2006.01)
C07C 47/198 (2006.01)

(52) U.S. Cl. ............. 514/263.36; 544/267; 548/326.5; 568/496

(58) Field of Classification Search ............. 544/267; 514/263.36
See application file for complete search history.

(56) References Cited

U.S. PATENT DOCUMENTS

| | | | |
|---|---|---|---|
| 3,135,753 A | 6/1964 | Hitchings et al. | |
| 4,657,910 A * | 4/1987 | Morgan | 514/263.36 |
| 4,820,709 A | 4/1989 | Hofer | |
| 5,173,491 A | 12/1992 | Kamoun et al. | |
| 5,453,426 A * | 9/1995 | Jacobson et al. | 514/263.23 |
| 5,489,598 A | 2/1996 | Connor et al. | |
| 5,716,967 A | 2/1998 | Kleinman | |
| 5,756,511 A | 5/1998 | West et al. | |
| 5,976,823 A | 11/1999 | Wu | |
| 6,025,361 A | 2/2000 | Cavalla et al. | |
| 6,046,019 A | 4/2000 | Goumeniouk et al. | |
| 6,066,641 A | 5/2000 | Cavalla et al. | |
| 6,294,541 B1 | 9/2001 | Cavalla et al. | |
| 6,319,928 B1 | 11/2001 | Chasin et al. | |
| 7,108,997 B2 | 9/2006 | Kettle | |
| 7,425,560 B2 * | 9/2008 | Tiden | 544/267 |
| 2004/0022871 A1 | 2/2004 | Mainnemare | |
| 2004/0029871 A1 | 2/2004 | Kettle et al. | |
| 2005/0070558 A1 | 3/2005 | Vidal Juan et al. | |
| 2005/0234036 A1 | 10/2005 | Hanson et al. | |
| 2007/0032468 A1 * | 2/2007 | Kettle et al. | 514/210.21 |
| 2007/0093483 A1 | 4/2007 | Svensson et al. | |
| 2008/0293748 A1 * | 11/2008 | Hanson et al. | 544/267 |
| 2009/0054468 A1 * | 2/2009 | Eriksson et al. | 514/263.21 |
| 2009/0131459 A1 * | 5/2009 | Tiden | 544/267 |
| 2009/0149475 A1 * | 6/2009 | Tiden et al. | 514/263.2 |

FOREIGN PATENT DOCUMENTS

| | | |
|---|---|---|
| CN | 1013676 | 8/1991 |
| EP | 0010531 | 6/1982 |
| EP | 0359505 | 3/1990 |
| EP | 0430300 | 6/1991 |
| EP | 0452926 | 3/1996 |
| EP | 01016407 | 5/2006 |
| JP | 02160235 | 6/1990 |
| WO | 8906125 | 7/1989 |
| WO | 9500516 A1 | 1/1995 |
| WO | 9618400 A1 | 6/1996 |
| WO | 9914204 | 3/1999 |
| WO | 9917773 A1 | 4/1999 |
| WO | 9936073 A1 | 7/1999 |
| WO | 9940091 | 8/1999 |
| WO | 0051598 A1 | 9/2000 |
| WO | 0059449 | 10/2000 |
| WO | 0185146 A1 | 11/2001 |
| WO | 0206272 | 1/2002 |
| WO | 0208237 A2 | 1/2002 |
| WO | 02066447 | 8/2002 |
| WO | 02090575 A1 | 11/2002 |
| WO | 03000694 | 1/2003 |
| WO | 03082873 | 10/2003 |
| WO | 03089430 A1 | 10/2003 |
| WO | 2004096781 | 11/2004 |
| WO | 2005037835 A1 | 4/2005 |
| WO | 2005042534 | 5/2005 |
| WO | 2005077950 A2 | 8/2005 |
| WO | 2006045564 A1 | 5/2006 |
| WO | 2006046910 | 5/2006 |
| WO | 2006062465 | 6/2006 |

OTHER PUBLICATIONS

Albert et al., "Reactive Chlorinating Species Produced by Myeloperoxidase Target the Vinyl Ether Bond of Plasmalogans," J. Biol. Chem., 2001, vol. 276(26), pp. 23733-23741.

(Continued)

*Primary Examiner* — Mark L Berch

(57) ABSTRACT

The present invention relates to a compound according to Formula (I)

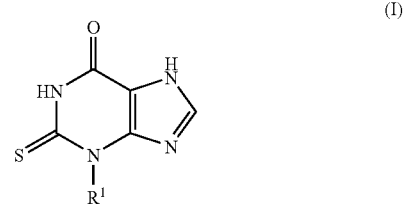

(I)

wherein $R^1$ is selected from $C_1$-$C_6$ alkyl, and said $C_1$-$C_6$ alkyl is substituted with $C_1$-$C_6$ alkoxy; and at least one of said $C_1$-$C_6$ alkyl or said $C_1$-$C_6$ alkoxy is branched; or a pharmaceutically acceptable salt thereof, solvate or solvate of a salt thereof, as well as, to compositions containing at least one compound according to Formula (I) and methods of treating at least one disease or condition therewith.

6 Claims, No Drawings

OTHER PUBLICATIONS

Imai et al., "Studies on Nucleic Acid Antagonists. VII. Synthesis and Characterization of 1,4,6-Triazaindenes (5H-Pyrrolo(3,2-d)pyrimidines)" Chem. Pharm. Bull., 1964, vol. 12, No. 9, pp. 1030-1042.

Kolasa et al., "Reactions of Alpha-Hydroxy Carbonyl Compounds With Azodicarboxylates and Triphenylphosphine: Synthesis of Alpha-N-Hydroxy Amino Acid Derivatives," Journal of Organic Chemistry, 1987, vol. 52, pp. 4978-4984.

Rao et al., "Synthesis of 5,7-Disubstituted-4-Beta-D-ribofuranosylpyrazolo[4,3-d]-pyrimidines and 2,4-Disubstituted-1-Beta-D-ribofuranosylpyrrolo[3,2-d]-pyrimidines as Congeners of Uridine and Cytidine," J. Heterocyclic Chemistry, 1992, vol. 29, pp. 343-354.

Co-Pending U.S. Appl. No. 11/577,833, filed Apr. 24, 2007.

Co-Pending U.S. Appl. No. 11/720,913, filed Jun. 5, 2007.

Aaron, S D et al., "Granulocyte Inflammatory Markers and Airway Infection during Acute Exacerbation of Chronic Obstructive Pulmonary Disease," Am J Respir Crit Care Med., 2001, pp. 349-355, vol. 163.

Akbiyik et al., "In vitro and in vivo inhibition of myeloperoxidase with 5-fluorouracil," Eur. J. Clin. Pharmacol., 2001, vol. 57, pp. 631-636.

Armitage et al., "Structure-Activity Relationships in a Series of 6-Thioxanthines with Bronchodilator and Coronary Dilator Properties," British Journal of Pharmacology and Chemotherapy (1961), vol. 17, pp. 196-207.

Baldus, S. et al., "Myeloperoxidase Serum Levels Predict Risk in Patients with Acute Coronary Syndromes," Circulation, 2003, pp. 1440-1445, vol. 108.

Berlow et al., "The Effect of Dapsone in Steroid-Dependent Asthma," 1991, J. Allergy Clin. Immunol., 1991, vol. 87(3), pp. 710-715.

Bozeman et al., "Inhibition of the human leukocyte enzymes myeloperoxidase and eosinophil peroxidase by dapsone," Biochemical Pharmacology, 1992, vol. 44, No. 3, pp. 553-563.

Brennan, M. et al., "Prognostic Value of Myeloperoxidase in Patients with Chest Pain," N Engl J Med., 2003, pp. 1595-1604, vol. 349, No. 17.

Choi, D-K et al., "Ablation of the Inflammatory Enzyme Myeloperoxidase Mitigates Features of Parkinson's Disease in Mice," J. Neurosci., 2005, pp. 6594-6600, vol. 25, No. 28.

Crooks, S W et al., "Bronchial Inflammation in Acute Bacterial Exacerbations of Chronic Bronchitis: the Role of Leukotriene B4," European Respiratory Journal, 2000, pp. 274-280, vol. 15, No. 2.

Cuzner, M L et al., "Plasminogen Activators and Matrix Metalloproteases, Mediators of Extracellular Proteolysis in Inflammatory Demyelination of the Central Nervous System," Journal of Neuroimmunology, 1999, pp. 1-14, vol. 94, No. 1-2.

Dallegri et al., Possible Modes of Action of Nimesulide in Controlling Neutrophilic Inflammation, Arzneimittel-Foschung/Drug Research, 1995, vol. 45(II), No. 10, pp. 1114-1117.

Daugherty, A. et al., "Myeloperoxidase, a Catalyst for Lipoprotein Oxidation, Is Expressed in Human Atherosclerotic Lesions," J Clin Invest., 1994, pp. 437-444, vol. 94, No. 1.

Fiorini, G. et al., "Serum ECP and MPO are Increased During Exacerbations of Chronic Bronchitis with Airway Obstruction," Biomedicine & Pharmacotherapy, 2000, pp. 274-278, vol. 54.

Garst et al., "Inhibition of Separated Forms of Phosphodiesterases from Pig Coronary Arteries by Uracils and by 7-Substituted Derivatives of 1-Methyl-3-isobutylxanthine," J. Med. Chem.; 1976; vol. 19(4) pp. 499-503.

Green, P S et al., "Neuronal Expression of Myeloperoxidase is Increased in Alzheimer's Disease," Journal of Neurochemistry, 2004, pp. 724-733, vol. 90, No. 3.

Grisham et al., "Assessment of Leukocye involvement during Ischemia and Reperfusion of Intestine," Am. J. Physiol., 1986, vol. 251, pp. 729-742.

Hampton, M B, et al., "Inside the Neutrophil Phagosome: Oxidants, Myeloperoxidase, and Bacterial Killing," Blood, 1998, pp. 3007-3017, vol. 92, No. 9.

Hope et al., "Large scale purification of myeloperoxidase from HL60 promyelocytic cells: characterization and comparison to human neutrophil myeloperoxidase," Protein Expression and Purification, 2000, vol. 18, pp. 269-276.

Jacobson et al., "1,3-Dialkylxanthine Derivatives Having High Potency as Antagonists at Human A2B Adenosine Receptors," Drug Development Research, 1999, vol. 47, pp. 45-53.

Katritzky et al., "A General Method for the N-Alkylation of Thioamides," Tetrahedron Letters, (1988), vol. 29(15), pp. 1755-1758.

Kettle et al., "Assays for the Chlorination Activity of Myeloperoxidase," Biophyl, 1992, vol. 296, pp. 502-512.

Kettle et al., "Mechanism of inhibition of myeloperoxidase by anti-inflammatory drugs," Biochemical Pharmacology, 1991, vol. 41, No. 10, pp. 1485-1492.

Kettle et al., "Superoxide is an Antagonist of Anti-Inflammatory Drugs that Inhibit Hypochlorous Acid Production by Myeloperoxidase," Biochemical Pharmacology, 1993, vol. 45, No. 10, pp. 2003-2010.

Khimicheskaya encyclopedia, ed. by Knunyants I.L., "Sovetskaya encyclopedia", 1990, V. 2, p. 1083.

English translation of Khimicheskaya encyclopedia, ed. by Knunyants I.L., "Sovetskaya encyclopedia", 1990, V. 2, p. 1083.

Kutter, D. et al., "Consequences of Total and Subtotal Myeloperoxidase Deficiency: Risk or Benefit?," Acta Haematol, 2000, pp. 10-15, vol. 104, No. 1.

Leckie et al., "Novel Therapy for COPD," Exp. Opin. Invest. Drugs, 2000, vol. 9(1), pp. 3-23.

Martin et al., "Reduction of Neutrophil-mediated injury to pulmonary endothelial cells by Dapsone 1-3", Am. Rev. Respir Dis., 1985, vol. 131, pp. 544-547.

Merlos et al., "Structure-Activity Relationships in a Series of Xanthine Derivatives with Antibronchoconstrictory and Bronchodilatory Activities," Eur. J. Med .Chem. Chim. Ther., 1990, vol. 25, pp. 653-658.

Nagra, R M, et al., "Immunohistochemical and Genetic Evidence of Myeloperoxidase Involvement in Multiple Sclerosis," Journal of Neuroimmunology, 1997, pp. 97-107, vol. 78, No. 1-2.

Nocker et al., "Interleukin-8 in Airway Inflammation in Patients with Chronic Asthma and Chronic Obstructive Pulmonary Disease," Int. Arch Allergy Immunol., 1996, vol. 109, pp. 183-191.

Ottonello et al., "Sulphonamides as Anti-Inflammatory Agents: Old Drugs for New Therapeutic Strategies in Neutrophilic Inflammation," Clinical Science, 1995, vol. 88, pp. 331-336.

Sugiyama, S. et al., "Macrophage Myeloperoxidase Regulation by Granulocyte Macrophage Colony-Stimulating Factor in Human Atherosclerosis and Implications in Acute Coronary Syndromes," Am J Pathol, 2001, pp. 879-891, vol. 158, No. 3.

Suzuki et al., "Assay method for myeloperoxidase in human polymorphonuclear leukocytes," Analytical Biochemistry, 1983, vol. 132, pp. 345-352.

Van Der Goot et al., "Isothiourea Analogues of Histamine as Potent Agonists or Antagonists of the Histamine H3-Receptor," Eur. J. Med. Chem., 1992, vol. 27, pp. 511-517.

Van Galen et al., "A Binding Site Model and Structure-Activity Relationships for the Rat A3 Adenosine Receptor," Molecular Pharmacology, 1994, vol. 45, pp. 1101-1111.

Van Zyl et al., "Interaction of methylxanthines with myeloperoxidase. An anti-inflammatory mechanism," Intnl J. of Biochem, 1992, vol. 24(6), pp. 929-935.

Woo et al., "Inhibitors of Human Purine Nucleoside Phosphorylase. Synthesis and Biological Activities of 8-Amino-3-benzylhypoxanthine and Related Analogues," J. Med. Chem., 1992; vol. 35, pp. 1451-1457.

Wooldridge et al., "The Synthesis of Some 6-Thioxanthines," J. Chem. Soc., 1962, pp. 1863-1868.

Zhang, R. et al.,"Association Between Myeloperoxidase Levels and Risk of Coronary Artery Disease," Jama, 2001, pp. 2136-2142, vol. 286, No. 17.

STN Intnl, CAPLUS Accession No. 1968:434597, Doc No. 69:34597, Dietz et al., "The hypnotic properties of 8-ethylthio-6-thiotheophylline sodium" & Toxicology and Applied Pharm., 1968, vol. 12, pp. 202-206.

STN Intnl, CAPLUS Accession No. 1966:420839, Doc No. 65:20839, Dietz et al., "The synthesis and pharmacologic evaluation of a series of 8-alkylthio-thiated theophyylines" & J. of Med Chem., 1966, vol. 9(4), pp. 500-506.

STN Intnl, CAPLUS Accession No. 1966:35888, Doc No. 64:35888, Dietz et al., "Synthesis of some 8-alkylthio-2-thiotheophyllines and 8-alkylthio-6-thiotheophyllines" & J. of Med Chem., 1966, vol. 9(1), p. 160.

STN Intnl CAPLUS Accession No. 1974:82889, No. 80:82889, Reichman, Uri et al., "Tautomerism, ionization and methylation of 2(methylthio)- and 2,8-bis(methyl-thio)hypoxanthines" & J. of the Chem. Soc., Perkin Transactions 1: Organic & BioOrganic Chem, 1972-1999, (22), 2647-55, 1973.

STN Intnl, File CAPLUS Accession No. 1984:630460, Doc No. 101:230460, Talukdar, P.B. et al., "Studies on ring-fused mesoionic thiazolo(3,2-a) imidazolo(4,5-d)pyrimidine derivatives," & Indian J. of Chem, Section B: Organic Chem. Including Medicinal Chem, 23B(4), pp. 316-320, 1984.

International Search Report issued for PCT/SE2007/000537, which is the PCT counterpart of U.S. Appl. No. 11/756,967, on Sep. 10, 2007.

English abstract of CN 1013676, STN International CAPLUS 1986:626214, (1986).

Non-final Office Action issued for U.S. Appl. No. 10/511,537 on Apr. 27, 2007 (U.S. Appl. No. 10/511,537 published as U.S. publication No. 2005-0234036, which is cited on the accompying SB08a Form).

*Ex Parte Quayle* Office Action issued for U.S. Appl. No. 10/511,537 on Aug. 27, 2007(U.S. Appl. No. 10/511,537 published as U.S. publication No. 2005-0234036, which is cited on the accompying SB08a Form).

Advisory Action issued for U.S. Appl. No. 10/275,824 on May 22, 2007 (U.S. Appl. No. 10/275,824, which is now abandoned, published as U.S. publication No. 2004-0029871, which is cited on the accompying SB08a Form).

Final OA issued for U.S. Appl. No. 10/275,824 on Feb. 8, 2007 (U.S. Appl. No. 10/275,824, which is now abandoned, published as U.S. publication No. 2004-0029871, which is cited on the accompying SB08a Form).

Non-final OA issued for U.S. Appl. No. 10/275,824 on Jun. 19, 2006 (U.S. Appl. No. 10/275,824, which is now abandoned, published as U.S. publication No. 2004-0029871, which is cited on the accompying SB08a Form).

Advisory Action issued for U.S. Appl. No. 10/275,824 on Mar. 15, 2006 (U.S. Appl. No. 10/275,824, which is now abandoned, published as U.S. publication No. 2004-0029871, which is cited on the accompying SB08a Form).

Final OA issued for U.S. Appl. No. 10/275,824 on Nov. 30, 2005 (U.S. Appl. No. 10/275,824, which is now abandoned, published as U.S. publication No. 2004-0029871, which is cited on the accompying SB08a Form).

Non-final OA issued for U.S. Appl. No. 10/275,824 on Jun. 17, 2005 (U.S. Appl. No. 10/275,824, which is now abandoned, published as U.S. publication No. 2004-0029871, which is cited on the accompying SB08a Form).

\* cited by examiner

2 THIOXANTHINE DERIVATIVES ACTING AS MPO-INHIBITORS

CROSS-REFERENCE TO RELATED APPLICATIONS

This application claims the benefit of U.S. Provisional Application No. 60/810,919, filed Jun. 5, 2006, the contents of which are hereby incorporated herein by reference.

The present invention relates to novel thioxanthine derivatives, compositions containing them and their use in therapy.

Myeloperoxidase (MPO) is a heme-containing enzyme found predominantly in polymorphonuclear leukocytes (PMNs). MPO is one member of a diverse protein family of mammalian peroxidases that also includes eosinophil peroxidase, thyroid peroxidase, salivary peroxidase, lactoperoxidase, prostaglandin H synthase, and others. The mature enzyme is a dimer of identical halves. Each half molecule contains a covalently bound heme that exhibits unusual spectral properties responsible for the characteristic green colour of MPO. Cleavage of the disulphide bridge linking the two halves of MPO yields the hemi-enzyme that exhibits spectral and catalytic properties indistinguishable from those of the intact enzyme. The enzyme uses hydrogen peroxide to oxidize chloride to hypochlorous acid. Other halides and pseudohalides (like thiocyanate) are also physiological substrates to MPO.

PMNs are of particular importance for combating infections. These cells contain MPO, with well-documented microbicidal action. PMNs act non-specifically by phagocytosis to engulf microorganisms, incorporate them into vacuoles, termed phagosomes, which fuse with granules containing myeloperoxidase to form phagolysosomes. In phagolysosomes the enzymatic activity of the myeloperoxidase leads to the formation of hypochlorous acid, a potent bactericidal compound. Hypochlorous acid is oxidizing in itself, and reacts most avidly with thiols and thioethers, but also converts amines into chloramines, and chlorinates aromatic amino acids. Macrophages are large phagocytic cells which, like PMNs, are capable of phagocytosing microorganisms. Macrophages can generate hydrogen peroxide and upon activation also produce myeloperoxidase. MPO and hydrogen peroxide can also be released to the outside of the cells where the reaction with chloride can induce damage to adjacent tissue.

Linkage of myeloperoxidase activity to disease has been implicated in neurological diseases with a neuroinflammatory response including multiple sclerosis, Alzheimer's disease, Parkinson's disease and stroke as well as other inflammatory diseases or conditions like asthma, chronic obstructive pulmonary disease, cystic fibrosis, atherosclerosis, ischemic heart disease, heart failure, inflammatory bowel disease, renal glomerular damage and rheumatoid arthritis. Lung cancer has also been suggested to be associated with high MPO levels.

Multiple Sclerosis (MS)

MPO positive cells are immensely present in the circulation and in tissue undergoing inflammation. More specifically MPO containing macrophages and microglia has been documented in the CNS during disease; multiple sclerosis (Nagra R M, et al. Journal of Neuroimmunology 1997; 78(1-2):97-107), Parkinson's disease (Choi D-K. et al. J. Neurosci. 2005; 25(28):6594-600) and Alzheimer's disease (Green P S. et al. Journal of Neurochemistry. 2004; 90(3):724-33). It is supposed that some aspects of a chronic ongoing inflammation result in an overwhelming destruction where agents from MPO reactions have an important role.

The enzyme is released both extracellularly as well as into phagolysosomes in the neutrophils (Hampton M B, Kettle A J, Winterbourn C C. Blood 1998; 92(9): 3007-17). A prerequisite for the MPO activity is the presence of hydrogen peroxide, generated by NADPH oxidase and a subsequent superoxide dismutation. The oxidized enzyme is capable to use a plethora of different substrates of which chloride is most recognized. From this reaction the strong non-radical oxidant—hypochlorous acid (HOCl)—is formed. HOCl oxidizes sulphur containing amino acids like cysteine and methionine very efficiently (Peskin A V, Winterbourn C C. Free Radical Biology and Medicine 2001; 30(5): 572-9). It also forms chloramines with amino groups, both in proteins and other biomolecules (Peskin A V. et al. Free Radical Biology and Medicine 2004; 37(10): 1622-30). It chlorinates phenols (like tyrosine) (Hazen S L. et al. Mass Free Radical Biology and Medicine 1997; 23(6): 909-16) and unsaturated bonds in lipids (Albert C J. et al. J. Biol. Chem. 2001; 276 (26): 23733-41), oxidizes iron centers (Rosen H, Klebanoff S J. Journal of Biological Chemistry 1982; 257(22): 13731-354) and crosslinks proteins (Fu X, Mueller D M, Heinecke J W. Biochemistry 2002; 41(4): 1293-301).

Proteolytic cascades participate both in cell infiltration through the BBB as well as the destruction of BBB, myelin and nerve cells (Cuzner M L, Opdenakker G. Journal of Neuroimmunology 1999; 94(1-2): 1-14; Yong V W. et al. Nature Reviews Neuroscience accomplished through the action of upstream proteases in a cascade as well as through oxidation of a disulfide bridge Fu X. et al. J. Biol. Chem. 2001; 276(44): 41279-87; Gu Z. et al. Science 2002; 297 (5584): 1186-90). This oxidation can be either a nitrosylation or HOCl-mediated oxidation. Both reactions can be a consequence of MPO activity. Several reports have suggested a role for MMP's in general and MMP-9 in particular as influencing cell infiltration as well as tissue damage (BBB breakdown and demyelination), both in MS and EAE (for review see Yong V W. et al, supra). The importance of these specific kinds of mechanisms in MS comes from studies where increased activity and presence of proteases have been identified in MS brain tissue and CSF. Supportive data has also been generated by doing EAE studies with mice deficient in some of the proteases implicated to participate in the MS pathology, or by using pharmacological approaches. The demyelination is supposed to be dependent on the cytotoxic T-cells and toxic products generated by activated phagocytes (Lassmann H. J Neurol Neurosurg Psychiatry 2003; 74(6): 695-7). The axonal loss is thus influenced by proteases and reactive oxygen and nitrogen intermediates. When MPO is present it will obviously have the capability of both activating proteases (directly as well as through disinhibition by influencing protease inhibitors) and generating reactive species.

Chronic Obstructive Pulmonary Disease (COPD)

Chronic obstructive pulmonary disease (COPD) is a disease state characterised by airflow limitation that is not fully reversible. The airflow limitation is usually both progressive and associated with an abnormal inflammatory response of the lungs to noxious particles or gases. COPD is a major public health problem. It is the fourth leading cause of chronic morbidity and mortality in the United States and is projected to rank fifth in 2020 as a worldwide burden of disease. In the UK the prevalence of COPD is 1.7% in men and 1.4% in women. COPD spans a range of severity from mild to very severe, with the cost of treatment rising rapidly as the severity increases.

Levels of MPO in sputum and BAL are much greater in COPD patients than normal, nonsmoking controls (Keatings V. M., Barnes P. J. Am. J Respir Crit. Care Med 1997; 155:

449-453; Pesci, A. et al. Eur Respir J 1998; 12:380-386). MPO levels are further elevated during exacerbations of the disease (Fiorini G. et al. Biomedicine & Pharmacotherapy 2000; 54:274-278; Crooks S. W. et al. European Respiratory Journal. 15(2): 274-80, 2000). The role of MPO is likely to be more important in exacerbations of COPD (Sharon S. D. et al. Am J Respir Crit. Care Med. 2001; 163: 349-355).

In addition to the destructive capacity of MPO there is a strong clinical link with vascular disease (Baldus S. et al. Circulation 2003; 108: 1440-5). Dysfunctional MPO polymorphisms are associated with a reduced risk of mortality from coronary artery disease (Nikpoor B. et al. Am Heart J 2001; 142: 336), and patients with high serum levels of MPO have increased risk of acute coronary syndrome. The effects of MPO on vascular disease may extend to COPD, since there is strong evidence that the pulmonary vasculature is one of the earliest sites of involvement in the smokers' lung. Striking changes in the intima of the pulmonary arteries have been described which show a dose relationship with smoking (Hale K. A., Niewoehner D. E., Cosio M. G. Am Rev Resp Dis 1980; 122: 273-8). The physiological function of MPO is associated with innate host defence. This role, however, is not critical as most cases of MPO deficient patients have relatively benign symptoms (Parry M. F. et al. Ann Int Med. 1981; 95: 293-301, Yang, K. D., Hill, H. R. Pediatr Infect Dis J. 2001; 20: 889-900). In summary, there is considerable evidence that elevated MPO levels in COPD may contribute to the disease via several mechanisms. A selective inhibitor of MPO would therefore be expected to alleviate both the acute and chronic inflammatory aspects of COPD and may reduce the development of emphysema.

Atherosclerosis

An MPO inhibitor should reduce the atherosclerotic burden and/or the vulnerability of existing atherosclerotic lesions and thereby decrease the risk of acute myocardial infarction, unstable angina or stroke, and reduce ischemia/reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al. (1994) J Clin Invest 94(1): 437-44). In eroded and ruptured human lesions, as compared to fatty streaks, an increased number of MPO expressing macrophages have been demonstrated, suggesting a particular role for MPO in acute coronary syndromes (Sugiyama, S. et al. (2001) Am J Pathol 158(3): 879-91). Patients with established coronary artery disease have higher plasma and leukocyte MPO levels than healthy controls (Zhang, R. et al. (2001) Jama 286(17): 2136-42). Moreover, in two large prospective studies plasma levels of MPO predicted the risk of future coronary events or revascularisation (Baldus, S. et al. (2003) Circulation 108(12):1440-5; Brennan, M. et al. (2003) N Engl J Med 349(17): 1595-604). Total MPO deficiency in humans has a prevalece prevalence of 1 in 2000-4000 individuals. These individuals appear principally healthy but a few cases of severe Candida infection have been reported. Interestingly, MPO deficient humans are less affected by cardiovascular disease than controls with normal MPO levels (Kutter, D. et al. (2000) Acta Haematol 104(1)). A polymorphism in the MPO promoter affects expression leading to high and low MPO expressing individuals. In three different studies the high expression genotype has been associated with an increased risk of cardiovascular disease (Nikpoor, B. et al. (2001) Am Heart J 142(2): 336-9; Makela, R., P. J. Karhunen, et al. (2003) Lab Invest 83(7): 919-25; Asselbergs, F. W., et al. (2004) Am J Med 116(6): 429-30). Data accumulated during the last ten years indicate that the proatherogenic actions of MPO include oxidation of lipoproteins, induction of endothelial dysfunction via consuming nitric oxide and destabilisation of atherosclerotic lesions by activation of proteases (Nicholls, S. J. and S. L. Hazen (2005) Arterioscler Thromb Vasc Biol 25(6): 1102-11). Recently, several studies have focused on nitro- and chlorotyrosine modifications of LDL and HDL lipoproteins. Since chlorotyrosine modifications in vivo only can be generated by hypochlorus acid produced by MPO these modifications are regarded as specific markers of MPO activity (Hazen, S. L. and J. W. Heinecke (1997) J Clin Invest 99(9): 2075-81). LDL particles exposed to MPO in vitro become aggregated, leading to facilitated uptake via macrophage scavenger receptors and foam cell formation (Hazell, L. J. and R. Stocker (1993) Biochem J 290 (Pt 1): 165-72). Chlorotyrosine modification of apoA1, the main apolipoprotein of HDL cholesterol, results in impaired cholesterol acceptor function (Bergt, C., S. et al. (2004) Proc Natl Acad Sci USA; Zheng, L. et al. (2004) J Clin Invest 114(4): 529-41).

Systematic studies of these mechanisms have shown that MPO binds to and travels with apoA1 in plasma. Moreover, MPO specifically targets those tyrosine residues of apoA1 that physically interact with the macrophage ABCA1 cassette transporter during cholesterol efflux from the macrophage (Bergt, C. et al. (2004) J Biol Chem 279(9): 7856-66; Shao, B. et al. (2005) J Biol Chem 280(7): 5983-93; Zheng et al. (2005) J Biol Chem 280(1): 38-47). Thus, MPO seems to have a dual aggravating role in atherosclerotic lesions, i.e. increasing lipid accumulation via aggregation of LDL particles and decreasing the reverse cholesterol transport via attack on the HDL protein apoA1.

The present invention discloses novel thioxanthines that display useful properties as inhibitors of the enzyme MPO. Furthermore, the novel compounds of the present invention display either one or more than one of the following: (i) improved selectivity towards TPO; (ii) unexpectedly high inhibitory activity towards MPO; (iii) improved brain permeability; (iv) improved solubility and/or (v) improved half-life; when compared to known thioxanthines. Such thioxanthines are disclosed in e.g. WO 03/089430 and WO 05/037835.

The present invention provides a compound according to Formula (I)

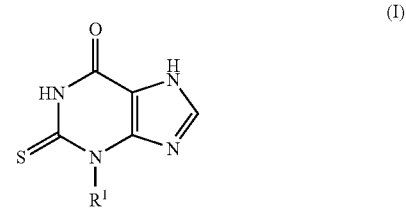

wherein
$R^1$ is selected from $C_1$-$C_6$ alkyl, and said $C_1$-$C_6$ alkyl is substituted with $C_1$-$C_6$ alkoxy; and at least one of said $C_1$-$C_6$ alkyl or said $C_1$-$C_6$ alkoxy is branched;
or a pharmaceutically acceptable salt thereof, solvate or solvate of a salt thereof.

According to one aspect of the present invention, the $C_1$-$C_6$ alkyl of $R^1$ represents $C_{2-4}$alkyl.

According to one embodiment of the present invention, said alkyl is selected from isobutyl, ethyl and propyl.

According to one embodiment of the present invention, said alkyl is substituted with $C_{1-3}$alkoxy.

According to one embodiment of the present invention, said alkyl is substituted with $C_1$-alkoxy.

According to one embodiment of the present invention, said alkyl is substituted with $C_2$-alkoxy.

According to one embodiment of the present invention, said alkyl is substituted with propoxy or iso-propoxy.

The present invention also relates to a compound selected from the group consisting of:
3-(2-Ethoxy-2-methylpropyl)-2-thioxanthine;
3-(2-Propoxy-2-methylpropyl)-2-thioxanthine;
3-(2-Methoxy-2-methylpropyl)-2-thioxanthine;
3-(2-isopropoxyethyl)-2-thioxanthine;
3-(2-Ethoxypropyl)-2-thioxanthine;
3-(2S-Ethoxypropyl)-2-thioxanthine;
3-(2R-Ethoxypropyl)-2-thioxanthine;
or a pharmaceutically acceptable salt, solvate or solvate of a salt thereof.

The compounds of Formula (I) may exist in tauomeric forms. All such tautomers and mixtures of tautomers are included within the scope of the present invention.

The compounds of Formula (I) may exist in enantiomeric forms. It is to be understood that all enantiomers, diastereomers, racemates and mixtures thereof are included within the scope of the invention.

Unless otherwise indicated, the term "$C_1$-$C_6$ alkyl" referred to herein denotes a straight or branched chain alkyl group having from 1 to 6 carbon atoms. Examples of such groups include methyl, ethyl, n-propyl, n-butyl, iso-butyl, tert-butyl, pentyl and hexyl. The term "$C_2$-$C_4$ alkyl" is to be interpreted analogously. It is to be understood that when the alkyl denotes a $C_1$ or a $C_2$ alkyl, such alkyls cannot be branched.

Unless otherwise indicated, the term "$C_1$-$C_6$ alkoxy" referred to herein denotes a straight or branched chain alkoxy group having from 1 to 6 carbon atoms. Examples of such groups include methoxy, ethoxy, 1-propoxy, 2-propoxy, 1-butoxy, iso-butoxy, tert-butoxy and pentoxy. The term "$C_1$-$C_3$ alkoxy" is to be interpreted analogously. It is to be understood that when the alkoxy denotes a $C_1$ or a $C_2$-alkoxy, such alkoxys cannot be branched. The present invention also relates to the use of the novel compounds of Formula (I) or a pharmaceutically acceptable salt thereof as a medicament.

A further aspect of the present invention is the use of a compound of Formula (I), or a pharmaceutically acceptable salt thereof, solvate or solvate of a salt thereof, in the manufacture of a medicament, for the treatment or prophylaxis of diseases or conditions in which inhibition of the enzyme MPO is beneficial.

A further aspect of the present invention provides the use of a compound of Formula (I), or a pharmaceutically acceptable salt thereof, solvate or solvate of a salt thereof, in the manufacture of a medicament, for the treatment or prophylaxis of neuroinflammatory disorders, cardio- and cerebrovascular atherosclerotic disorders and peripheral artery disease, heart failure and respiratory disorders such as chronic obstructive pulmonary disease (COPD).

Another further aspect of the present invention provides the use of a compound of Formula (I), or a pharmaceutically acceptable salt thereof, solvate or solvate of a salt thereof, in the manufacture of a medicament, for the treatment or prophylaxis of multiple sclerosis. Treatment may include slowing progression of disease.

Another further aspect of the present invention provides the use of a compound of Formula (I), or a pharmaceutically acceptable salt thereof, solvate or solvate of a salt thereof, in the manufacture of a medicament, for the treatment or prophylaxis of Parkinson's disease. Treatment may include slowing progression of disease.

Another further aspect of the present invention provides the use of a compound of Formula (I) or a pharmaceutically acceptable salt thereof, solvate or solvate of a salt thereof, in the manufacture of a medicament, for the treatment or prophylaxis of atherosclerosis by preventing and/or reducing the formation of new atherosclerotic lesions or plaques and/or by preventing or slowing progression of existing lesions and plaques.

Another further aspect of the present invention provides the use of a compound of Formula (I) or a pharmaceutically acceptable salt thereof, solvate or solvate of a salt thereof, in the manufacture of a medicament, for the treatment or prophylaxis of atherosclerosis by changing the composition of the plaques to reduce the risk of plaque rupture and atherothrombotic events.

Another further aspect of the present invention provides the use of a compound of Formula (I) or a pharmaceutically acceptable salt thereof, solvate or solvate of a salt thereof, in the manufacture of a medicament, for the treatment or prophylaxis of respiratory disorders, such as chronic obstructive pulmonary disease. Treatment may include slowing progression of disease.

According to the present invention, there is also provided a method of treating, or reducing the risk of, diseases or conditions in which inhibition of the enzyme MPO is beneficial which comprises administering to a person suffering from or at risk of, said disease or condition, a therapeutically effective amount of a compound of Formula (I), or a pharmaceutically acceptable salt thereof, solvate or solvate of a salt thereof.

Further, there is also provided a method of treating, or reducing the risk of, neuroinflammatory disorders, cardio- and cerebrovascular atherosclerotic disorders or peripheral artery disease, or heart failure or respiratory disorders, such as chronic obstructive pulmonary disease (COPD), in a person suffering from or at risk of, said disease or condition, wherein the method comprises administering to the person a therapeutically effective amount of a compound of Formula (I), or a pharmaceutically acceptable salt thereof, solvate or solvate of a salt thereof.

Further, there is also provided a method of treating, or reducing the risk of, multiple sclerosis in a person suffering from or at risk of, said disease or condition, wherein the method comprises administering to the person a therapeutically effective amount of a compound of Formula (I), or a pharmaceutically acceptable salt thereof, solvate or solvate of a salt thereof.

Further, there is also provided a method of treating, or reducing the risk of, Parkinson's disease in a person suffering from or at risk of, said disease or condition, wherein the method comprises administering to the person a therapeutically effective amount of a compound of Formula (I), or a pharmaceutically acceptable salt thereof. There is also provided a method of treating, or reducing the risk of atherosclerosis by preventing and/or reducing the formation of new atherosclerotic lesions or plaques and/or by preventing or slowing progression of existing lesions and plaques in a person suffering from or at risk of, said disease or condition, wherein the method comprises administering to the person a therapeutically effective amount of a compound of Formula (I) or a pharmaceutically acceptable salt thereof, solvate or solvate of a salt thereof.

There is also provided a method of treating, or reducing the risk of atherosclerosis by changing the composition of the plaques so as to reduce the risk of plaque rupture and atherothrombotic events in a person suffering from or at risk of, said disease or condition, wherein the method comprises administering to the person a therapeutically effective amount of a compound of Formula (I) or a pharmaceutically acceptable salt thereof, solvate or solvate of a salt thereof.

In another aspect the present invention provides a pharmaceutical formulation comprising a therapeutically effective amount of a compound of Formula (I), or a pharmaceutically acceptable salt thereof, solvate or solvate of a salt thereof, in admixture with a pharmaceutically acceptable adjuvant, diluent or carrier, for use in the treatment or prophylaxis of diseases or conditions in which inhibition of the enzyme MPO is beneficial.

In a further aspect the present invention provides a pharmaceutical formulation comprising a therapeutically effective amount of a compound of Formula (I), or a pharmaceutically acceptable salt thereof, solvate or solvate of a salt thereof, in admixture with a pharmaceutically acceptable adjuvant, diluent or carrier, for use in the treatment or prophylaxis of neuroinflammatory disorders.

In a further aspect the present invention provides a pharmaceutical formulation comprising a therapeutically effective amount of a compound of Formula (I), or a pharmaceutically acceptable salt thereof, in admixture with a pharmaceutically acceptable adjuvant, diluent or carrier, for use in the treatment or prophylaxis of multiple sclerosis, cardio- and cerebrovascular atherosclerotic disorders and peripheral artery disease and heart failure and respiratory disorders, such as chronic obstructive pulmonary disease. In another aspect the present invention provides a pharmaceutical formulation comprising a therapeutically effective amount of a compound of Formula (I), or a pharmaceutically acceptable salt thereof, solvate or solvate of a salt thereof, in admixture with a pharmaceutically acceptable adjuvant, diluent or carrier, for use in the treatment or prophylaxis of atherosclerosis by preventing and reducing the formation of new atherosclerotic lesions and/or plaques and/or by preventing or slowing progression of existing lesions and plaques.

In another aspect the present invention provides a pharmaceutical formulation comprising a therapeutically effective amount of a compound of Formula (I), or a pharmaceutically acceptable salt thereof, solvate or solvate of a salt thereof, in admixture with a pharmaceutically acceptable adjuvant, diluent or carrier, for use in the treatment or prophylaxis of atherosclerosis by changing the composition of the plaques so as to reduce the risk of plaque rupture and atherothrombotic events.

The present invention further relates to therapies for the treatment of: Neurodegenerative Disorder(s) including but not limited to Alzheimer's Disease (AD), Dementia, Cognitive Deficit in Schizophrenia (CDS), Mild Cognitive Impairment (MCI), Age-Associated Memory Impairment (AAMI), Age-Related Cognitive Decline (ARCD), Cognitive Impairement No Dementia (CIND), Multiple Sclerosis, Parkinson's Disease (PD), postencephalitic parkinsonism, Huntington's Disease, amyotrophic lateral sclerosis (ALS), motor neuron diseases (MND), Multiple System Atrophy (MSA), Corticobasal Degeneration, Progressive Supranuclear Paresis, Guillain-Barré Syndrome (GBS), and Chronic Inflammatory Demyelinating Polyneuropathy (CIDP). Dementia includes, but is not limited to, Down syndrome, vascular dementia, dementia with Lewy bodies, HIV dementia, Frontotemporal dementia Parkinson's Type (FTDP), Pick's Disease, Niemann-Pick's Disease, traumatic brain injury (TBI), dementia pugilistica, Creutzfeld-Jacob Disease and prion diseases.

The present invention further relates to therapies for the treatment of: Neuroinflammatory Disorder(s) including but not limited to Multiple Sclerosis (MS), Parkinson's disease, Multiple System Atrophy (MSA), Corticobasal Degeneration, Progressive Supranuclear Paresis, Guillain-Barré Syndrome (GBS), chronic inflammatory demyelinating polyneuropathy (CIDP). Multiple sclerosis (MS) includes Relapse Remitting Multiple Sclerosis (RRMS), Secondary Progressive Multiple Sclerosis (SPMS), and Primary Progressive Multiple Sclerosis (PPMS).

The present invention further relates to therapies for the treatment of: Cognitive Disorder(s) including but not limited to
a) Dementia, including but not limited to Alzheimer's Disease (AD), Down syndrome, vascular dementia, Parkinson's Disease (PD), postencephelatic parkinsonism, dementia with Lewy bodies, HIV dementia, Huntington's Disease, amyotrophic lateral sclerosis (ALS), motor neuron diseases (MND), Frontotemporal dementia Parkinson's Type (FTDP), progressive supranuclear palsy (PSP), Pick's Disease, Niemann-Pick's Disease, corticobasal degeneration, traumatic brain injury (TBI), dementia pugilistica, Creutzfeld-Jacob Disease and prion diseases;
b) Cognitive Deficit in Schizophrenia (CDS);
c) Mild Cognitive Impairment (MCI);
d) Age-Associated Memory Impairment (AAMI);
e) Age-Related Cognitive Decline (ARCD);
f) Cognitive Impairement No Dementia (CIND).

The present invention further relates to therapies for the treatment of: Attention-Deficit and Disruptive Behavior Disorder(s) including but not limited to attention deficit disorder (ADD), attention deficit hyperactivity disorder (ADHD) and affective disorders.

The present invention also relates to the treatment of the diseases and conditions below which may be treated with the compounds of the present invention:
respiratory tract: obstructive diseases of the airways including: asthma, including bronchial, allergic, intrinsic, extrinsic, exercise-induced, drug-induced (including aspirin and NSAID-induced) and dust-induced asthma, both intermittent and persistent and of all severities, and other causes of airway hyper-responsiveness; chronic obstructive pulmonary disease (COPD); bronchitis, including infectious and eosinophilic bronchitis; emphysema; bronchiectasis; cystic fibrosis; sarcoidosis; farmer's lung and related diseases; hypersensitivity pneumonitis; lung fibrosis, including cryptogenic fibrosing alveolitis, idiopathic interstitial pneumonias, fibrosis complicating anti-neoplastic therapy and chronic infection, including tuberculosis and aspergillosis and other fungal infections; complications of lung transplantation; vasculitic and thrombotic disorders of the lung vasculature, and pulmonary hypertension; antitussive activity including treatment of chronic cough associated with inflammatory and secretory conditions of the airways, and iatrogenic cough; acute and chronic rhinitis including rhinitis medicamentosa, and vasomotor rhinitis; perennial and seasonal allergic rhinitis including rhinitis nervosa (hay fever); nasal polyposis; acute viral infection including the common cold, and infection due to respiratory syncytial virus, influenza, coronavirus (including SARS) and adenovirus; bone and joints: arthritides associated with or including osteoarthritis/osteoarthrosis, both primary and secondary to, for example, congenital hip dysplasia; cervical and lumbar spondylitis, and low back and neck pain; rheumatoid arthritis and Still's disease; seronegative spondyloarthropathies including ankylosing spondylitis, psoriatic arthritis, reactive arthritis and undifferentiated spondarthropathy; septic arthritis and other infection related arthopathies and bone disorders such as tuberculosis, including Potts' disease and Poncet's syndrome; acute and chronic crystal-induced synovitis including urate gout, calcium pyrophosphate deposition disease, and calcium apatite related tendon, bursal and synovial inflammation; Behcet's disease; primary and secondary Sjogren's syndrome; systemic sclerosis and limited scleroderma; systemic lupus erythematosus, mixed connective tissue disease, and undifferentiated connective tissue disease; inflammatory myopathies including dermatomyositits and polymyositis; polymalgia rheumatica; juvenile arthritis including idiopathic inflammatory arthritides of whatever joint distribution and associated syndromes, and rheumatic fever and its systemic ic complications; vasculitides including giant cell arteritis, Takayasu's arteritis, Churg-Strauss syndrome, polyarteritis nodosa, microscopic polyarteritis, and vasculitides associated with viral infection, hypersensitivity reactions, cryoglobulins, and paraproteins; low back pain; Familial Mediterranean fever, Muckle-Wells syndrome, and Familial Hibernian Fever, Kikuchi disease; drug-induced arthalgias, tendonititides, and myopathies;

The present invention further relates to combination therapies wherein a compound of Formula (I) or a pharmaceutically acceptable salt thereof, or a pharmaceutical composition or formulation comprising a compound of Formula (I) is administered concurrently or sequentially with therapy and/or an agent for the treatment of any one of cardio- and cerebrovascular atherosclerotic disorders and peripheral artery disease.

The present invention includes compounds of Formula (I) and also said compounds in their form of salts. Suitable salts include those formed with organic or inorganic acids or organic or inorganic bases. Such salts will normally be pharmaceutically acceptable although salts of non-pharmaceutically acceptable acids or bases may be of utility in the preparation and purification of the compound in question. Thus, acid addition salts include inter alia those formed from hydrochloric acid. Base addition salts include those in which the cation is inter alia sodium or potassium.

The compounds of the invention and intermediates thereto may be isolated from their reaction mixtures and, if necessary further purified, by using standard techniques.

The compounds of Formula (I) may exist in enantiomeric forms. Therefore, all enantiomers, diastereomers, racemates, tautomers and mixtures thereof are included within the scope of the invention. The various optical isomers may be isolated by separation of a racemic mixture of the compounds using conventional techniques, for example, fractional crystallisation, or HPLC. Alternatively, the various optical isomers may be prepared directly using optically active starting materials.

The compounds of Formula (I) and their pharmaceutically acceptable salts are useful because they possess pharmacological activity as inhibitors of the enzyme MPO.

For the above-mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of Formula (I) and pharmaceutically acceptable derivatives thereof, may be used on their own, or in the form of appropriate pharmaceutical compositions in which the compound or derivative is in admixture with a pharmaceutically acceptable adjuvant, diluent or carrier. Thus, another embodiment of the invention concerns a pharmaceutical composition comprising a novel compound of Formula (I), or a pharmaceutically acceptable salt thereof, in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of Formula (I), or a pharmaceutically acceptable salt thereof.

There is also provided a process for the preparation of such a pharmaceutical composition, which comprises mixing the ingredients.

A compound of Formula (I) or a pharmaceutically acceptable salt thereof may be administered in association with compounds from one or more of the following groups:
1) anti-inflammatory agents, for example
   a) NSAIDs (e.g. acetylsalicylic acid, Ibuprofen, naproxen, flurbiprofen, diclofenac, indometacin);
   b) leukotriene synthesis inhibitors (5-LO inhibitors e.g. AZD4407, Zileuton, licofelone, CJ13610, CJ13454; FLAP inhibitors e.g. BAY-Y-1015, DG-031, MK591, MK886, A81834; LTA4 hydrolase inhibitors e.g. SC56938, SC57461A);
   c) leukotriene receptor antagonists (e.g. CP195543, amelubant, LY293111, accolate, MK571);
2) anti-hypertensive agents, for example
   a) beta-blockers (e.g. metoprolol, atenolol, sotalol);
   b) angiotensin converting enzyme inhibitors (e.g. captopril, ramipril, quinapril, enalapril);
   c) calcium channel blockers (e.g. verapamil, diltiazem, felodipine, amlodipine);
   d) angiotensin II receptor antagonists (e.g. irbesartan, candesartan, telemisartan, losartan);
3) anti-coagulantia, for example
   a) thrombin inhibitors (e.g. ximelagatran), heparines, factor Xa inhibitors;
   b) platelet aggregation inhibitors (e.g. clopidrogrel, ticlopidine, prasugrel, AZD6140);
4) modulators of lipid metabolism, for example
   a) insulin sensitizers such as PPAR agonists (e.g. pioglitazone, rosiglitazone, Galida, muraglitazaar, gefemrozil, fenofibrate);
   b) HMG-CoA reductase inhibitors, statins (e.g. simvastatin, pravastatin, atorvastatin, rosuvastatin, fluvastatin);
   c) cholesterol absorption inhibitors (e.g. ezetimibe);
   d) IBAT inhibitors (e.g. AZD-7806);
   e) LXR agonists (e.g. GW-683965A, T-0901317);
   f) FXR receptor modulators;
   g) phospholipase inhibitors;
5) anti-anginal agents, for example, nitrates and nitrites;
6) modulators of oxidative stress, for example, anti-oxidants (e.g. probucol, AGI 1067).

Methods of Preparation

According to the invention, we further provide a process for the preparation of compounds of Formula (I), or a pharmaceutically acceptable salt, solvate, enantiomer, diastereomer or racemate thereof wherein $R^1$ is defined as in Formula (I).

Throughout the following description of such processes it is to be understood that, where appropriate, suitable protecting groups will be added to, and subsequently removed from, the various reactants and intermediates in a manner that will be readily understood by one skilled in the art of organic synthesis. Conventional procedures for using such protecting groups as well as examples of suitable protecting groups are described, for example, in "Protective Groups in Organic Synthesis", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to the one skilled in the art of organic synthesis. Examples of transformations are given below, and it is to be understood that the described transformations are not limited only to the generic groups or substituents for which the transformations are exemplified. References and descriptions on other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "Advanced Organic Chemistry", March 4th ed. McGraw Hill (1992) or, "Organic Synthesis", Smith, McGraw Hill, (1994). Techniques for purification of intermediates and final products include for example, straight and reversed phase chromatography on column or rotating plate, recrystallisation, distillation and liquid-liquid or solid-liquid extraction, which will be readily understood by one skilled in the art. The definitions of substituents and groups are as in Formula (I) except where defined differently. The terms "room temperature" and "ambient temperature" shall mean, unless otherwise specified, a temperature between 16 and 25° C. The term "reflux" shall mean, unless otherwise stated, in reference to an employed solvent using a temperature at or slightly above the boiling point of the named solvent. It is understood that microwaves can be used for the heating of reaction mixtures. The terms "flash chromatography" or "flash column chromatography" shall mean preparative chromatography on silica using an organic solvent, or mixtures thereof, as mobile phase.

Preparation of End Products

1. A process for preparing a compound of Formula (I), wherein $R^1$ is defined as in Formula (I) is shown in Scheme 1:

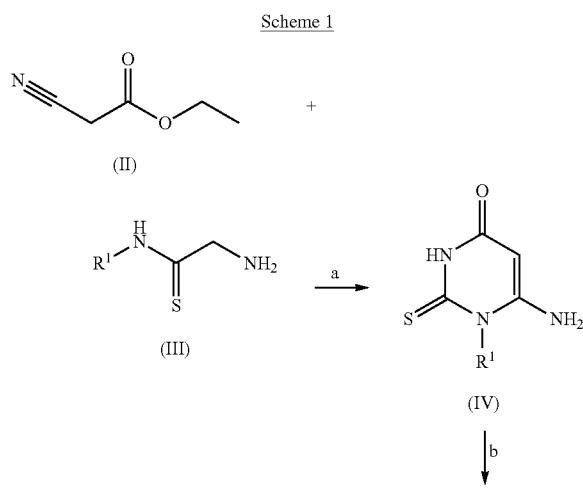

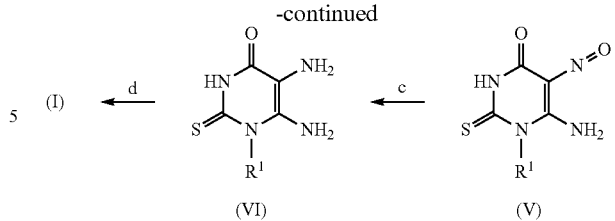

Compounds of formula (II), (III), (IV), (V) and (VI) are useful intermediates in the preparation of compound of Formula (I) wherein $R^1$ is defined as in Formula (I). Compounds of formula (II)-(VI) are either commercially available, or can be prepared from either commercially available, or in the literature described compounds (Ouwerkerk et al. Eur. J. Org. Chem. 2002, 14, 2356).

a) Reaction of ethyl cyanoacetate (II) with a thiourea of formula (III), wherein $R^1$ is defined as in Formula (I). In the process, ethyl cyanoacetate (II) and an appropriate thiourea (III) are dissolved or suspended in a suitable alcohol, such as ethanol, and an alkoxide, such as sodium ethoxide, is added. The temperature is typically from 70° C. up to reflux temperature of the reaction mixture.

b) Reaction of a thiouracil of formula (IV), wherein $R^1$ is defined above with sodium nitrite in an acidic solution. In the process, the thiouracil (IV) is suspended in a solvent such as acetic acid (10 to 100% in aqueous solution) and hydrochloric acid (aq. 1M) and stirred at a suitable temperature between 0° C. and 85° C. for 10 to 20 minutes before the sodium nitrite, dissolved in water, is added dropwise.

c) Reduction of a nitroso compound of formula (V), wherein $R^1$ is defined above. In the process, the reduction of the nitroso compound of formula (V) may be carried out with a suitable reducing agent, such as sodium dithionite or gaseous hydrogen ($H_2$ (gas)), in a suitable solvent mixture such as water and ammonia solution or sodium hydroxide (aq. 1N) at a temperature range between room temperature and 75° C. for 30 minutes to 24 hours. Alternatively the sodium dithionite could be added directly to the conditions used in step b.

d) The reaction of a diamine of formula (VI), wherein $R^1$ is defined above with i) formic acid, ii) formamidine acetate or with iii) trialkylorthoester is described below:

(i) In process (d), the diamine of formula (VI) is treated with formic acid (98%), at a suitable temperature between ambient temperature and the reflux temperature of the reaction mixture. The process is continued for a suitable period of time, typically for between 20 to 30 minutes. After removal of the formic acid, treatment with a suitable aqueous base, for example, with 10% aqueous sodium hydroxide solution, then yields the compound of Formula (I). The treatment with base is carried out for a suitable time at a suitable temperature, for example for about 30 minutes to 90 minutes at a temperature between ambient temperature and the reflux temperature of the reaction mixture. Alternatively the reaction can be performed in a solvent such as water to which formic acid and sulphuric acid is added. The reaction is then heated under reflux overnight which after neutralization gives the compound of Formula (I).

(ii) In process (d), the diamine of formula (VI) is treated with formamidine acetate in a solvent such as (DMSO) dimethyl sulfoxide at a suitable temperature, for example 70° C., until the reaction is complete, typically for 1-3 h.

(iii) In process (d), the diamine of formula (VI) is treated at a suitable temperature with an excess of an appropriate ortho ester such as triethylorthoformate and tripropylorthoformate, optionally in the presence of a suitable solvent such as an alcohol, until reaction is complete. The temperature is typically up to the reflux temperature of the reaction mixture, and reaction times are generally from 30 minutes to overnight.

Other methods for the conversion of a diamine of formula (VI) into a compound of Formula (I) are described in the literature and will be readily known to the person skilled in the art.

2. A process for preparing a compound of Formula (I), wherein $R^1$ is defined as in Formula (I) (Suzuki et al. Chem. Pharm. Bull. 2002, 50, 1163) is shown in Scheme 2

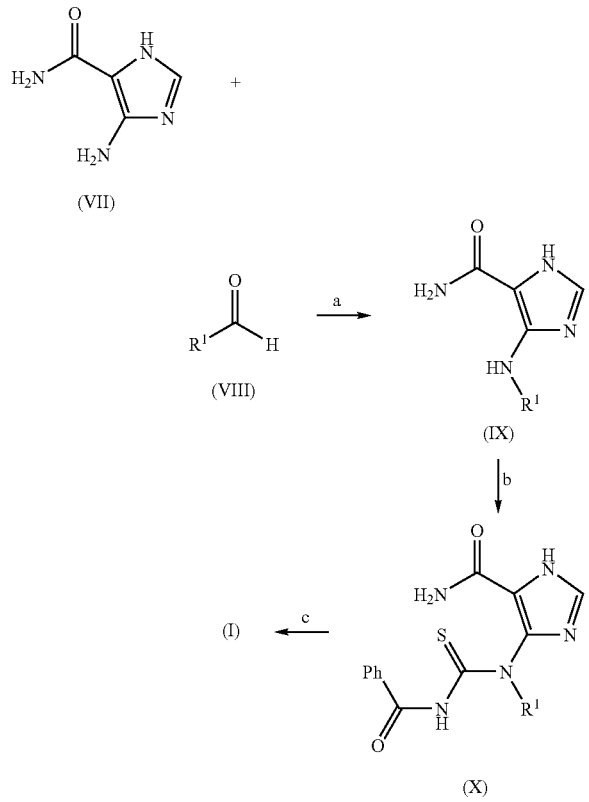

Compounds of formula (VII), (VIII), (IX) and (X) are useful intermediates in the preparation of compounds of Formula (I) wherein R1 is defined as in Formula (I). Compounds of formula (VII)-(X) are either commercially available, or can be prepared from either commercially available, or in the literature described compounds.

a) Reaction of 5-Amino-4-imidazolecarboxamide (VII) with an appropriate aldehyde of formula (VIII), wherein $R^1$ is defined as in Formula (I), and a suitable borohydride, such as sodium cyanoborohydride or sodium acetoxyborohydride, in a suitable solvent such as methanol, with the optional addition of acetic acid, at room temperature or with heating up 10 to 50° C. gave the intermediate of formula (IX).

b) Reaction of intermediate of formula (IX), wherein $R^1$ is defined as in Formula (I), with an isothiocyanate such as benzoylisothiocyanate or ethoxycarbonyl isothiocyanate in a solvent such as dichloromethane and methanol at room temperature gave intermediate of formula (X).

c) Reaction of intermediate of formula (X), wherein $R^1$ is defined as in Formula (I), with a base such as sodium hydroxide or ammonia (7N in methanol) at a temperature ambient to 80° C. and the reflux temperature of the solvent gave a compound of formula (I) wherein $R^1$ is defined as in Formula (I).

General Methods

All solvents used were analytical grade and commercially available anhydrous solvents were routinely used for reactions. Reactions were typically run under an inert atmosphere of nitrogen or argon.

$^1$H and $^{13}$C NMR spectra were recorded at 400 MHz for proton and 100 MHz for carbon-13 either on a VARIAN® Unity+400 NMR Spectrometer equipped with a 5 mm BBO probe head with Z-gradients, or a BRUKER® Avance 400 NMR spectrometer equipped with a 60 µl dual inverse flow probe head with Z-gradients, or a BRUKER® DPX400 NMR spectrometer equipped with a 4-nucleus probe head equipped with Z-gradients. Unless specifically noted in the examples, spectra were recorded at 400 MHz for proton and 100 MHz for carbon-13. The following reference signals were used: the middle line of DMSO-$d_6$ δ 2.50 ($^1$H), δ 39.51 ($^{13}$C); the middle line of CD$_3$OD δ 3.31 ($^1$H) or δ 49.15 ($^{13}$C); acetone-$d_6$ 2.04 ($^1$H), 206.5 ($^{13}$C); and CDCl$_3$ δ 7.26 ($^1$H), the middle line of CDCl$_3$ δ 77.16 ($^{13}$C) (unless otherwise indicated).

Mass spectra were recorded on a WATERS® LCMS consisting of an ALLIANCE® 2795 (LC), WATERS® PDA 2996, and ELS® detector (Sedex 75) and a ZMD® single quadrupole mass spectrometer. The mass spectrometer was equipped with an electrospray ion source (ES) operated in a positive or negative ion mode. The capillary voltage was 3 kV and cone voltage was 30 V. The mass spectrometer was scanned between m/z 100-600 with a scan time of 0.7 s. The column temperature was set to 40° C. The Diode Array Detector was scanned from 200-400 nm. The temperature of the ELS detector was adjusted to 40° C. and the pressure was set to 1.9 bar. For LC separation a linear gradient was applied starting at 100% A (A: 10 mM ammonium acetate (NH$_4$OAc) in 5% acetonitrile (MeCN)) and ending at 100% B (B: MeCN) after four minutes. The column used was a X-TERRA® MS C8, 3.0×50; 3.5 µm (Waters) run at 1.0 mL/min.

Alternatively, mass spectra was performed on a GC-MS (GC 6890, 5973N MSD) supplied by AGILENT TECHNOLOGIES®. The column used was a VF-5® MS, ID 0.25 mm×30 m, 0.25 µm (Varian Inc.). A linear temperature gradient was applied starting at 40° C. (hold 1 min) and ending at 300° C. (hold 1 min), 25° C./minute. The MS was equipped with a CI ion source and the reactant gas was methane. The MS was scanned between m/z 50-500 and the scan speed was set to 3.25 scan/s. The MS was equipped with an EI ion source. The MS was scanned between m/z 50-500 and the scan speed was set to 3.25 scan/s. The electron voltage was set to 70 eV.

HPLC analyses were performed on an AGILENT® HP1100 system consisting of G1379A MICRO VACUUM DEGASSER®, G1312A BINARY PUMP®, G1367A WELL PLATE® auto-sampler, G1316A THERMOSTATTED COLUMN COMPARTMENT® and G1315B DIODE ARRAY DETECTOR®. Column: X-TERRA® MS, WATERS®, 3.0×100 mm, 3.5 µm. The column temperature was set to 40° C. and the flow rate to 1.0 ml/min. The Diode Array Detector was scanned from 210-300 nm, step and peak width were set to 2 nm and 0.05 min, respectively. A linear gradient was applied, starting at 100% A (A: 10 mM NH$_4$OAc in 5% MeCN) and ending at 100% B (B: MeCN), in 6 min.

GC-MS analysis was performed on a GC 6890, 5973N MSD, supplied by AGILENT TECHNOLOGIES®. The column used was a VF-5® MS, ID 0.25 mm×30 m, 0.25 µm (VARIAN® Inc.). A linear temperature gradient was applied starting at 40° C. (hold 1 min) and ending at 300° C. (hold 1 min), 25° C./minute. The MS was equipped with a CI ion source and the reactant gas was methane. The MS was scanned between m/z 50-500 and the scan speed was set to 3.25 scan/s. The electron voltage was set to 70 eV.

Microwave heating was performed in an INITIATOR® or SMITH SYNTHESIZER® Single-mode microwave cavity producing continuous irradiation at 2450 MHz.

A typical workup procedure after a reaction consisted of extraction of the product with a solvent such as ethyl acetate, washing with water followed by drying of the organic phase over Magnesium sulphate ($MgSO_4$) or Sodium sulphate ($Na_2SO_4$) filtration and concentration of the solution in vacuo.

Thin layer chromatography (TLC) was performed on MERCK® TLC-plates (Silica gel 60 F254) and UV visualized the spots. Flash chromatography was preformed on a COMBIFLASH® COMPANION® using REDISEP® normal-phase flash columns. Typical solvents used for flash chromatography were mixtures of chloroform/methanol, dichloromethane/methanol and heptane/ethyl acetate.

Preparative chromatography was run on a WATERS® autopurification HPLC with a diode array detector. Column: X-TERRA® MS C8, 19×300 mm, 10 μm. Narrow gradients with MeCN/(95:5 0.1M $NH_4OAc$:MeCN) were used at a flow rate of 20 ml/min. Alternatively, another column was used; ATLANTIS® C18 19×100 mm, 5 μm column. Gradient with acetonitrile/0.1M ammonium acetate in 5% acetonitrile in MILLIQ WATER®, run from 0% to 35-50% acetonitrile, in 15 min. Flow rate: 15 ml/min. Alternatively, purification was achieved on a semi preparative SHIMADZU® LC-8A HPLC with a SHIMADZU® SPD-10A UV vis.-detector equipped with a WATERS SYMMETRY® column (C18, 5 μm, 100 mm×19 mm).

Narrow gradients with MeCN/0.1% trifluoroacetic acid in MILLIQ WATER® were used at a flow rate of 10 ml/min.

The following abbreviations have been used:
aq. aqueous;
m-CPBA 3-chloroperoxybenzoic acid;
equiv. equivalent;
DEAD diethyl azodicarboxylate
DMF N,N-dimethylformamide;
DMSO dimethylsulfoxide;
HOAc acetic acid;
$NaCNBH_3$ sodium cyanoborohydride;
$Na_2SO_4$ sodium sulphate;
r.t. room temperature;
o.n. over night;
THF tetrahydrofuran;
$Boc_2O$ Di-tert-butyl dicarbonate;
MeOH methanol;
EtOH ethanol;
EtOAc ethylacetate;
TFA trifluoroacetic acid;
DIPEA N,N-Diisopropylethylamine;
$CH_2Cl_2$ methylene chloride;
$CHCl_3$ chloroform;
TEMPO 2,2,6,6-tetramethyl-1-piperidinyloxy;
HCl acetic acid Starting materials used were either available from commercial sources or prepared according to literature procedures and had experimental data in accordance with those reported.

EXAMPLES

The invention is illustrated, but in no way limited, by the following examples:

Example 1

3-(2-Ethoxy-2-methylpropyl)-2-thioxanthine (a) 2-Bromo-1,1-diethoxy-2-methylpropane The product was synthesized according to a modified procedure described in U.S. Pat. No. 3,652,579.

Bromine water (2.95 mL, 57.6 mmol) was added drop by drop to isobutyraldehyde (4.82 g, 66.8 mmol) in EtOH (22 mL) and the resulting mixture was stirred at r.t. for 40 minutes. More bromine water (0.3 mL, 5.86 mmol) was added. The reaction mixture was neutralized by the addition of calcium carbonate (3.5 g, 25.3 mmol). The remaining calcium carbonate was filtered off and the filtrate was poured onto ice-water mixture. The aqueous phase was extracted with $CH_2Cl_2$, dried $Na_2SO_4$, filtered and concentrated. After vacuum distillation the title product was obtained in 67% (10.10 g) yield.

$^1$H NMR (400 MHz, DMSO-$d_6$) δ ppm 4.43 (s, 1H), 3.80-3.73 (m, 2H), 1.64 (s, 6H), 1.15 (t, 6H).

(b) 2-Ethoxy-2-methylpropanal

The product was synthesized according to a procedure described in U.S. Pat. No. 3,652,579.

2-Bromo-1,1-diethoxy-2-methylpropane (5.63 g, 25 mmol) obtained from 1a was added drop by drop to potassium bitartrate (2.35 g, 12.5 mmol) in refluxing deionized water (22.5 mL) over 50 minutes. The resulting mixture was left to reflux for 1 h 10 minutes. The solvent and product was distilled off. ammonium sulphate (totally 8.5 g) was added to the product-solvent mixture. The mixture was stirred for a while. The two phases were separated and the upper phase was distilled from calcium chloride yielding 55% (1.60 g) of the title product. MS (CI) m/z 117 (M+1).

(c) 4-[(2-Ethoxy-2-methylpropyl)amino]-1H-imidazole-5-carboxamide $NaCNBH_3$ (0.077 g, 1.23 mmol) was added to 5-amino-4-imidazolecarboxamide hydrochloride (0.200 g, 1.23 mmol) and acetic acid (141 μL, 2.46 mmol) in methanol (1.5 mL). 2-Ethoxy-2-methylpropanal (0.286 g, 2.46 mmol) obtained from Example 1(b) was added drop by drop. After 1.5 h more 2-Ethoxy-2-methylpropanal (0.300 g, 2.58 mmol) was added followed by more 2-Ethoxy-2-methylpropanal after 0.5 h (0.424 mg, 3.65 mmol). The reaction mixture was stirred at r.t. 17 h after which it was concentrated and purified by flash silica gel chromatography ($CHCl_3$/MeOH; 20:1-9.1), to give the title compound as an oil in 90% yield (0.251 g). MS (ESI) m/z 227 (M+1).

(d) 3-(2-Ethoxy-2-methylpropyl)-2-thioxanthine

Ethoxycarbonyl isothiocyanate (0.171 g, 1.30 mmol) was added to a stirred solution of 4-[(2-Ethoxy-2-methylpropyl)amino]-1H-imidazole-5-carboxamide (0.246 g, 1.09 mmol), which had been obtained from Example 1(c), in $CH_2Cl_2$ (1.1 mL) at r.t. for 0.5 h, then the reaction was left unstirred at 4° C. for 16 h. The reaction mixture was heated to r.t. for 1 h and the solvent was evaporated, the residue was dissolved in 2% sodium hydroxide (aq.) (27 mL) and the reaction was heated at 50° C. for 5.5 h. The pH was adjusted to neutral with conc. HCl and 1M HCl. The precipitate was collected by filtration, washed with water and purified by flash silica gel chromatography (CHCl$_3$/MeOH; 20:1), to give the title compound in 47% yield (96 mg).

$^1$H NMR (400 MHz, DMSO-d$_6$) δ ppm 13.76 (br s, 1H), 12.42 (s, 1H), 8.13 (s, 1H), 4.69 (br s, 2H), 3.54 (q, 2H), 1.21 (s, 6H), 1.02 (t, 3H). MS (ESI) m/z 267 (M−1).

Example 2

3-(2-Propoxy-2-methylpropyl)-2-thioxanthine (a) 2-Bromo-2-methyl-1,1-dipropoxypropane 2-Bromo-2-methyl-1,1-dipropoxypropane was prepared according to a modified method described in U.S. Pat. No. 3,652,579.

Isobutyraldehyde (7.2 g, 0.10 mol) and 1-propanol (12 mL) were cooled in an icebath. Bromine (4.4 mL, 0.086 mol) was added drop-by-drop during 20 min. Stirring was continued at ambient temperature for 5 min and then at 55° C. for 30 min. Calcium carbonate (3 g, 0.030 mol) was added in portions. The resulting mixture was stirred at ambient temperature for 1 h. The mixture was filtered and the solids were washed with diethyl ether. Water (15 mL) was then added. The organic phase was separated, dried over sodium sulphate and concentrated in vacuo at ambient temperature. This crude product (13.5 g, 53%) was used in the next step without further purification.

$^1$H NMR (CDCl$_3$) δ ppm 4.40 (s, 1H), 3.73-3.79 (m, 2H), 3.51-3.57 (m, 2H), 1.73 (s, 6H), 1.60-1.66 (m, 4H), 0.93-0.97 (m, 6H).

(b) 2-Methyl-2-propoxypropanol

2-Methyl-2-propoxypropanol was prepared according to a modified method described in U.S. Pat. No. 3,652,579. A slurry consisting of 2-bromo-2-methyl-1,1-dipropoxypropane obtained from Example 2(a) (6.5 g, 0.026 mol), potassium hydrogen tartrate (4.8 g, 0.026 mol) in water (75 mL) was heated at reflux for 7 h. A distillation set-up was mounted and the liquid that was distilled between 82-90° C. was collected. The organic phase was separated. The obtained crude product (1.9 g, 56%) was used without further purification.

$^1$H NMR (CDCl$_3$) δ ppm 9.58 (s, 1H), 3.31-3.34 (m, 2H), 1.54-1.64 (m, 2H), 1.26 (s, 6H), 0.92-0.96 (m, 3H).

(c) 4-[(2-Methyl-2-propoxypropyl)amino]-1H-imidazole-5-carboxamide

The reaction mixture of 2-methyl-2-propoxypropanol, which was obtained from Example 2(b), (1.0 g, 8.3 mmol), 5-amino-4-imidazolecarboxamide (0.5 g, 4.0 mmol), sodium cyanoborohydride (0.25 g, 4.0 mmol) and acetic acid (0.45 mL, 7.9 mmol) in 10 mL of methanol was stirred at ambient temperature for 1 h. The solvent was removed in vacuo. Water (20 mL) and ethyl acetate (20 mL) were added. The organic phase was separated and the solvent was removed in vacuo. Purification by ISCO flash (EtOAc:Heptane, gradient elution 1:1 to 100% EtOAc) gave 0.19 g (20%) of the title compound.

$^1$H NMR (CDCl$_3$) δ ppm 6.98 (s, 1H), 6.39 (br s, 1H), 3.40 (t, 2H, J=6.7 Hz), 3.14 (d, 2H, J=4.3 Hz), 1.56-1.65 (m, 2H), 1.22 (s, 6H), 0.95 (t, 3H, J=7.5 Hz); MS (ESI) m/z 241 (M+1).

(d) 3-(2-Propoxy-2-methylpropyl)-2-thioxanthine

4-[(2-Methyl-2-propoxypropyl)amino]-1H-imidazole-5-carboxamide obtained from Example 2(c) was dissolved (0.19 g, 0.78 mmol) in 7 mL of dichloromethane. The obtained solution was stirred at ambient temperature. Benzoyl isothiocyanate (0.50 g, 3.1 mmol) was added in portions during 6 h. The reaction mixture was stirred overnight and the solvent was then removed in vacuo. Ammonia in methanol (7 mL of 7 M solution) was added and the obtained solution was heated at 50° C. for 3 h and then at 80° C. for 3 h in a pressure flask. The cooled reaction mixture was concentrated and the crude product was purified by reverse phase HPLC. The product was obtained in 22% (48 mg) yield.

$^1$H NMR (DMSO-d$_6$) δ ppm 13.70 (very br s, 1H), 12.39 (br s, 1H), 8.12 (s, 1H), 4.69 (br s, 2H), 3.41 (t, 2H, J=6.6 Hz), 1.36-1.44 (m, 2H), 1.21 (s, 6H), 0.81 (t, 3H, J=7.5 Hz);

$^{13}$C NMR (DMSO-d$_6$) δ ppm 175.3, 152.5, 149.9, 140.7, 111.0, 75.9, 62.7, 53.5, 25.4, 23.2, 10.6; MS (ESI) m/z 283 (M+1).

Example 3

3-(2-Methoxy-2-methylpropyl)-2-thioxanthine (a) 2-Methoxy-2-methylpropanal

The product was synthesized according to a procedure described in U.S. Pat. No. 3,652,579.

(b) 4-[(2-Methoxy-2-methylpropyl)amino]-1H-imidazole-5-carboxamide

5-Amino-4-imidazolecarboxamide hydrochloride (0.162 g, 1.0 mmol) and 2-methoxy-2-methylpropanal, which was obtained from Example 3(a) (0.204 g, 2.0 mmol) were mixed in methanol (3 mL) at r.t. Acetic acid (141 μL, 2.46 mmol) mL) was then added and the mixture was allowed to stir for 30 min followed by addition of NaCNBH$_3$ (0.063 g, 1.0 mmol). After 3 h, additional 2-methoxy-2-methylpropanal (0.060 g, 0.59 mmol) was added. The reaction mixture was stirred at r.t. for 17 h and was then concentrated and purified by flash silica gel chromatography (CHCl$_3$:MeOH=5:1). The title compound was obtained as an oil in 73% yield (0.155 g). MS (ESI) m/z 213 (M+1).

(c) 3-(2-Methoxy-2-methylpropyl)-2-thioxanthine

Ethoxycarbonyl isothiocyanate (0.144 g, 1.1 mmol) was added to a stirred solution of 4-[(2-methoxy-2-methylpropyl)amino]-1H-imidazole-5-carboxamide (0.155 g, 0.73 mmol), which was obtained from Example 3(b), in CH$_2$Cl$_2$ (2.5 mL) at r.t. for 16 h. The solvent was evaporated and the residue was then dissolved in 2% aqueous sodium hydroxide (NaOH) solution (10 mL) and heated at 50° C. for 3 h. The pH was adjusted to neutral with 2 M HCl and the resulted precipitates were collected by filtration followed by prep-HPLC purification. The title compound was obtained as a white solid in 32% yield (60 mg).

$^1$H NMR (400 MHz, DMSO-d$_6$) δ ppm 12.41 (s, 1H), 8.13 (s, 1H), 4.68 (s, 2H), 3.21 (s, 3H), 1.20 (s, 6H). MS (ESI) m/z 255 (M+1).

Example 4

3-(2-isopropoxyethyl)-2-thioxanthine (a) 4-[(2-isopropoxyethyl)amino]-1H-imidazole-5-carboxamide Trichlorocyanuric acid (1.23 g, 5.29 mmol) was added to a solution of 2-isopropoxyethanol (0.50 g, 4.80 mmol) in CH₂Cl₂ (3 mL). The reaction mixture was cooled to 0° C. and TEMPO (0.015 g, 0.09 mmol) was carefully added in small portions. The mixture was stirred at r.t. for 20 minutes and then filtrated through Celite and washed with CH₂Cl₂. The filtrate was kept cold, 0° C., during the filtration. The obtained aldehyde solution was added to a stirred mixture of 4-amino-1H-imidazole-5-carboxamide hydrochloride (0.78 g, 4.80 mmol), which was obtained from Example 3(b), at 0° C. in MeOH (5 mL). The mixture was stirred for 20 minutes, then NaCNBH₄ (0.30 g, 4.80 mmol) was added. After stirring at r.t for 5 h the mixture was concentrated and purified by flash chromatography (CH₂Cl₂/methanol gradient; 0 to 5% methanol), to yield the title compound (0.39 g, 38%) as an oil.

¹H NMR (DMSO-d₆) δ ppm 7.58-7.45 (1H, m), 6.84-6.66 (2H, m), 6.23 (1H, br s), 3.59-3.49 (1H, m), 3.49-3.43 (2H, m), 3.35-3.28 (2H, m), 1.10-1.06 (6H, m); MS (ESI) m/z 213 (M+1).

(b) 3-(2-isopropoxyethyl-2-thioxo-1,2,3,7-tetrahydro-6H-purin-6-one

4-[(2-isopropoxyethyl)amino]-1H-imidazole-5-carboxamide, which was obtained from Example 4(a) (0.37 g, 1.74 mmol) was dissolved in CH₂Cl₂ (5 mL).

Etoxycarbonylisothiocyanate (0.27 g, 2.09 mmol) was added and the mixture was stirred at r.t. for 30 minutes. The mixture was concentrated in vacuo and dissolved in 2M sodium hydroxide (2 mL). The reaction was run in the microwave at 120° C. for 10 minutes. The pH of the solution was adjusted to neutral pH with 2M HCl and the precipitate was collected by filtration and washed with water. Purified by preparative HPLC, obtaining the title compound (0.14 g, 32%) as a solid.

¹H NMR (DMSO-d₆) δ ppm 13.82 (1H, br s), 12.44 (1H, br s), 8.16 (1H, s), 4.72-4.51 (2H, m), 3.80-3.67 (2H, m), 3.67-3.56 (1H, m), 1.04 (6H, d, J=6.0 Hz); MS (ESI) m/z 255 (M+1).

Example 5

3-(2-Ethoxy-propyl)-2-thioxanthine (a) (2-Ethoxy-propyl)-thiourea

2-Ethoxy-propylamine (1.50 g, 14.5 mmol) and benzoylisothiocyanate (2.61 g, 16.0 mmol) in chloroform (50 mL) were heated at 75° C. for 1 h. The solvent was removed under reduced pressure and methanol (15 mL) and water (30 mL) were added. Potassium carbonate (2.0 g, 14.5 mmol) was added and the mixture was heated at 75° C. for 2 h. After cooling to room temperature, the mixture was neutralized with 2M sulphuric acid and the solvent was removed under reduced pressure. The crude product was dissolved in methanol and insoluble material was removed by filtration. The solvent was distilled off and the resulting solid was washed with dichloromethane and dissolved in ethanol. Insoluble material was removed by filtration and the solvent was removed under reduced pressure. This gave the title compound as a white solid (1.6 g, 59% yield).

¹H NMR (DMSO-d₆) δ ppm 7.52 (1H, broad s), 7.02 (2H, broad s), 3.58-3.33 (5H, m), 1.09 (3H, t, J=6.95 Hz), 1.03 (3H, d, J=6.06 Hz); MS (ES) m/z 161 (M−1).

(b) 6-Amino-1-(2-ethoxy-propyl)-2-thioxo-2,3-dihydro-1H-pyrimidin-4-one (2-Ethoxy-propyl)-thiourea (1.5 g, 1.4 mmol) obtained from Example 5(a) and ethyl cyanoactetate (1.75 g, 15.5 mmol) were added to a solution of sodium ethoxide [made from sodium (0.35 g, 15.2 mmol) and absolute ethanol (15 mL)]. The resulting mixture was refluxed for over night. After cooling to room temperature water was added and the ontained mixture was neutralized with 2 M sulphuric acid. The resulting precipitate was collected by filtration and the solid was washed with water to give the desired product (1.2 g, 71% yield).

¹H NMR (DMSO-d₆) δ ppm 11.86 (1H, broad s), 6.73 (2H, broad s), 4.91 (1H, s), 4.54 (1H, broad s), 4.00-3.85 (1H, m), 3.66-3.46 (1H, m), 3.39-3.23 (2H, m), 1.12 (3H, d, J=6.32 Hz), 1.03 (3H, t, J=7.07 Hz); MS (ES) m/z 230 (M+1).

(c) 6-Amino-1-(2-ethoxy-propyl)-5-nitroso-2-thioxo-2,3-dihydro-1H-pyrimidin-4-one 6-Amino-1-(2-ethoxy-propyl)-2-thioxo-2,3-dihydro-1H-pyrimidin-4-one (1.1 g, 4.8 mmol) obtained from Example 5b was suspended in 10% acetic acid (20 mL) and the mixture was stirred for 15 minutes. Sodium nitrite (0.36 g, 5.3 mmol) was added and the resulting mixture was heated at 75° C. for 1 h. The reaction mixture turned pink and then purple. The mixture was cooled to room temperature, and the purple solid was collected by filtration and washed with water to give the title compound (1.05 g, 70% yield). This solid was used in Example 5(d) without further purification.

¹H NMR (DMSO-d₆) δ ppm 13.16 (1H, broad s), 12.61 (1H, broad s), 4.50 (1H, broad s), 4.24 (1H, broads), 3.96-3.84 (1H, m), 3.56-3.43 (1H, m), 3.34-3.20 (2H, m), 1.13 (3H, d, J=6.32 Hz), 0.95 (3H, t, J=6.95 Hz); MS (ES) m/z 259 (M+1).

(d) 5,6-Diamino-1-(2-ethoxy-propyl)-2-thioxo-2,3-dihydro-1H-pyrimidin-4-one

6-Amino-1-(2-ethoxy-propyl)-5-nitroso-2-thioxo-2,3-dihydro-1H-pyrimidin-4-one (1.0 g, 3.9 mmol) obtained from Example 5(c) was suspended in 32% ammonia (5 mL) and water (10 mL) was added. This mixture was heated at 75° C. and sodium dithionite (1.7 g, 9.7 mmol) was added in small portions. After heating for another 5 minutes the reaction mixture was removed from the oil bath and stirred at ambient temperature for 2 h. The pH of the mixture was adjusted to neutral pH with 2M H₂SO₄. The solid was collected by filtration and washed with water and dried to yield the diamine (0.6 g, 41% yield). This product was used in Example 5(e) without further purification.

¹H NMR (DMSO-d₆) δ ppm 5.91 (2H, broad s), 4.59 (1H, broad s), 4.11 (1H, broad s), 3.99-3.85 (1H, m), 3.68-3.42 (3H, m), 3.39-3.20 (2H, m), 1.14 (3H, d, J=6.32 Hz), 1.03 (3H, t, J=6.95 Hz); MS (ES) m/z 245 (M+1).

(e) 3-(2-Ethoxy-propyl)-2-thioxanthine 5,6-Diamino-1-(2-ethoxy-propyl)-2-thioxo-2,3-dihydro-1H-pyrimidin-4-one (0.60 g, 2.45 mmol) obtained from Example 5(d) was suspended in formic acid (6 mL) and the obtained solution was heated at 70° C. for 2 h. Excess formic acid was evaporated off under reduced pressure. 10% sodium hydroxide (6 mL) was added to the solid and the obtained solution was heated at 70° C. for 2 h. The pH of the solution was adjusted to neutral pH with 2M sulphuric acid. The obtained precipitate was collected by filtration and washed with water. Purified by preparative HPLC, the title compound (0.18 g, 29% yield) was obtained as a solid.

¹H NMR (DMSO-d₆) δ ppm 13.77 (1H, broad s), 12.41 (1H, broad s), 8.13 (1H, s), 4.64-4.51 (1H, m), 4.47-4.33 (1H, m), 4.25-4.12 (1H, m), 3.58-3.42 (1H, m), 3.43-3.31 (1H, m), 1.06 (3H, d, J=6.32 Hz), 0.95 (3H, t, J=6.95 Hz); $^{13}$C NMR (DMSO-d$_6$) □ ppm 174.22, 152.96, 150.18, 141.54, 111.16, 71.15, 63.78, 52.13, 18.33, 15.80; MS (ES) m/z 255 (M+1).

Example 6

3-(2S-Ethoxy-propyl)-2-thioxanthine and 3-(2R-Ethoxy-propyl)-2-thioxanthine

A solution of racemic 3-(2-Ethoxy-propyl)-2-thioxanthine (5 mg/mL) obtained from example 6 was separated into its two enantiomers by using chiral HPLC on a Chiralpak AD column (21.2×250 mm; 10 µm). The mobile phase was 100% methanol and the flow rate 8 mL/min. The injection volume was 2 mL.

The first eluated enantiomer was 3-(2S-Ethoxy-propyl)-2-thioxanthine and this enantiomer was determined by single crystal diffraction technique at 200 K, e.e. 98%; MS (ES) m/z 255 (M+1).

The second eluated enantiomer was 3-(2R-Ethoxy-propyl)-2-thioxanthine, e.e. 98%; MS (ES) m/z 255 (M+1).
Screens Methods for the determination of MPO inhibitory activity are disclosed in patent application WO 02/090575. The pharmacological activity of compounds according to the invention was tested in the following screen in which the compounds were either tested alone or in the presence of added tyrosine:

Assay buffer: 20 mM sodium/potassium phosphate buffer pH 6.5 containing 10 mM taurine and 100 mM NaCl.

Developing reagent: 2 mM 3,3',5,5'-tetramethylbenzidine (TMB), 200 µM KI, 200 mM acetate buffer pH 5.4 with 20% DMF.

To 10 µl of diluted compounds in assay buffer, 40 µl of human MPO (final concentration 2.5 nM), with or without 20 µM tyrosine (final concentration, if present, 8 µM), was added and the mixture was incubated for 10 minutes at ambient temperature. Then 50 µl of H$_2$O$_2$ (final concentration 100 µM), or assay buffer alone as a control, were added. After incubation for 10 minutes at ambient temperature, the reaction was stopped by adding 10 µl 0.2 mg/ml of catalase (final concentration 18 µg/ml). The reaction mixture was left for an additional 5 minutes before 100 µl of TMB developing reagent was added. The amount of oxidised 3,3',5,5'-tetramethylbenzidine formed was then measured after about 5 minutes using absorbance spectroscopy at about 650 nM. IC$_{50}$ values were then determined using standard procedures.

When tested in at least one version of the above screen, the compounds of Examples 1 to 6 gave IC$_{50}$ values of less than 60 µM, indicating that they are expected to show useful therapeutic activity. A representative result is shown in the following Table.

| Compound | Inhibition of MPO (in the presence of tyrosine) IC$_{50}$ µM |
|---|---|
| Example 5 | 0.5 |

The invention claimed is:
1. A compound according to Formula (I)

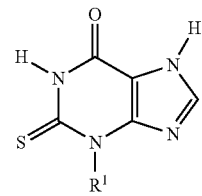

wherein:
R$^1$ is a C$_1$-C$_6$ alkyl substituted with a C$_1$-C$_6$ alkoxy;
and at least one of said C$_1$-C$_6$ alkyl or said C$_1$-C$_6$ alkoxy is branched;
or a pharmaceutically acceptable salt thereof.

2. The compound according to claim 1, wherein said alkyl is selected from isobutyl, ethyl and propyl.

3. The compound according to claim 1, wherein said alkyl is substituted with a C$_1$-C$_3$ alkoxy.

4. A compound selected from
3-(2-ethoxy-2-methylpropyl)-2-thioxanthine
3-(2-propoxy-2-methylpropyl)-2-thioxanthine
3-(2-methoxy-2-methylpropyl)-2-thioxanthine
3-(2-isopropoxyethyl)-2-thioxanthine
3-(2-ethoxypropyl)-2-thioxanthine
3-(2S-ethoxypropyl)-2-thioxanthine; and
3-(2R-ethoxypropyl)-2-thioxanthine
or a pharmaceutically acceptable salt thereof.

5. A pharmaceutical composition comprising a compound according to claim 1, or a pharmaceutically acceptable salt thereof, optionally in admixture with a pharmaceutically acceptable adjuvant, diluents or carrier.

6. The compound of claim 1, wherein:
C$_1$-C$_6$ alkyl is selected from methyl, ethyl, n-propyl, n-butyl, iso-propyl, tert-butyl, pentyl and hexyl;
C$_1$-C$_6$ alkoxy is selected from methoxy, ethoxy, 1-propoxy, 1-butoxy, iso-butoxy, tert-butoxy and pentoxy;
and at least one of said C$_1$-C$_6$ alkyl or said C$_1$-C$_6$ alkoxy is branched;
or a pharmaceutically acceptable salt thereof.

* * * * *